(12) United States Patent
Wu et al.

(10) Patent No.: US 9,778,162 B2
(45) Date of Patent: *Oct. 3, 2017

(54) WHITE BLOOD CELL ANALYSIS SYSTEM AND METHOD

(71) Applicant: Abbott Laboratories, Abbott Park, IL (US)

(72) Inventors: Jiong Wu, Los Gatos, CA (US); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 156 days.

This patent is subject to a terminal disclaimer.

(21) Appl. No.: 14/808,205

(22) Filed: Jul. 24, 2015

(65) Prior Publication Data

US 2016/0018310 A1   Jan. 21, 2016

Related U.S. Application Data

(63) Continuation of application No. 13/456,729, filed on Apr. 26, 2012, now Pat. No. 9,091,624.

(60) Provisional application No. 61/482,541, filed on May 4, 2011.

(51) Int. Cl.
| | |
|---|---|
| *G01N 15/14* | (2006.01) |
| *G01N 21/64* | (2006.01) |
| *G01N 15/10* | (2006.01) |
| *G01N 15/08* | (2006.01) |
| *G01N 33/49* | (2006.01) |
| G01N 15/00 | (2006.01) |

(52) U.S. Cl.
CPC ..... *G01N 15/1434* (2013.01); *G01N 15/1459* (2013.01); *G01N 21/6428* (2013.01); *G01N 33/49* (2013.01); *G01N 2015/008* (2013.01); *G01N 2015/1006* (2013.01); *G01N 2015/1477* (2013.01); *G01N 2015/1488* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 4,661,913 A | 4/1987 | Wu et al. | |
| 4,727,020 A | 2/1988 | Recktenwald | |
| 4,882,284 A | 11/1989 | Kirchanski et al. | |
| 5,559,037 A | 9/1996 | Kim et al. | |
| 5,631,165 A | 5/1997 | Chupp et al. | |
| 5,656,499 A | 8/1997 | Chupp et al. | |
| 5,776,709 A | 7/1998 | Jackson et al. | |
| 5,812,419 A | 9/1998 | Chupp et al. | |
| 5,879,900 A | 3/1999 | Kim et al. | |
| 5,891,734 A | 4/1999 | Gill et al. | |
| 5,928,949 A | 7/1999 | Sakata et al. | |
| 5,939,326 A | 8/1999 | Chupp et al. | |
| 6,197,593 B1 | 3/2001 | Deka et al. | |
| 6,228,652 B1 | 5/2001 | Rodriguez et al. | |
| 6,551,831 B2 | 4/2003 | Gupta et al. | |
| 7,299,135 B2 | 11/2007 | Thayer | |
| 7,638,290 B2 | 12/2009 | Lefevre et al. | |
| 2004/0265830 A1 | 12/2004 | Szabo et al. | |
| 2006/0269970 A1 | 11/2006 | Paul et al. | |
| 2007/0111276 A1 | 5/2007 | Lefevre et al. | |
| 2007/0287145 A1 | 12/2007 | Mizukami et al. | |
| 2007/0298408 A1 | 12/2007 | Mizukami et al. | |
| 2009/0023129 A1 | 1/2009 | Xu et al. | |
| 2009/0061478 A1 | 3/2009 | Poulsen et al. | |
| 2010/0273168 A1 | 10/2010 | Krockenberger et al. | |

FOREIGN PATENT DOCUMENTS

| | | |
|---|---|---|
| JP | H0599919 | 4/1993 |
| JP | H06501106 | 1/1994 |
| JP | H09508703 | 9/1997 |
| JP | H09508705 | 9/1997 |
| JP | 2938976 | 6/1999 |
| JP | 2000501838 | 2/2000 |
| JP | 2001091513 | 4/2001 |

(Continued)

OTHER PUBLICATIONS

BD LSR II Flow Cytometer Brochure, BD Biosciences (2003).
Champert et al. (2004) "White-light supercontinuum generation in normally dispersive optical fiber using original multi-wavelength pumping system" Optics Express 12(19):4366-4371.
De Grooth et al. (1987) "Light-Scattering Polarization Measurements as a New Parameter in Flow Cytometry" *Cytometry* 8:539-544.
Flowguide, Flow cytometry guide, abcam® (2013).
Flowguide, Introduction to Flow Cytometry: A Learning Guide, Technical Manual, BD Biosciences (Apr. 2000).
Fluorochromes, Table of Fluorochromes, SALK CCMI (2008).

(Continued)

*Primary Examiner* — Taeyoon Kim
*Assistant Examiner* — Srikanth Patury
(74) *Attorney, Agent, or Firm* — Edward J Baba; Bozicevic, Field & Francis LLP

(57) ABSTRACT

Systems and methods for analyzing blood samples, and more specifically for performing a white blood cell (WBC) differential analysis. The systems and methods screen WBCs by means of fluorescence staining and a fluorescence triggering strategy. As such, interference from unlyzed red blood cells (RBCs) and fragments of lysed RBCs is substantially eliminated. The systems and methods also enable development of relatively milder WBC reagent(s), suitable for assays of samples containing fragile WBCs. In one embodiment, the systems and methods include: (a) staining a blood sample with an exclusive cell membrane permeable fluorescent dye, which corresponds in emission spectrum to an excitation source of a hematology instrument; (b) using a fluorescence trigger to screen the blood sample for WBCs; and (c) using measurements of (1) axial light loss, (2) intermediate angle scatter, (3) 90° polarized side scatter, (4) 90° depolarized side scatter, and (5) fluorescence emission to perform a differentiation analysis.

15 Claims, 11 Drawing Sheets

(56) References Cited

FOREIGN PATENT DOCUMENTS

| | | |
|---|---|---|
| JP | 2003510557 | 3/2003 |
| JP | 2003310299 | 11/2003 |
| JP | 2008500558 | 1/2008 |
| JP | 2010513929 | 4/2010 |
| JP | 2011069707 | 4/2011 |
| JP | 2013592594 | 1/2013 |
| WO | 2009001868 | 12/2008 |
| WO | 2010011583 | 1/2010 |
| WO | 2011028437 | 3/2011 |

OTHER PUBLICATIONS

LTAC Preservatives Handbook, 2013.
McCoy et al. (1991) "Sorting Minor Subpopulations of Cells: Use of Fluorescence as the Triggering Signal" *Cytometry* 12:268-274.
Sakata (2000) "Reagent Characteristics in the XE-2100 NRBC Channel" Sysmex Journal International, Technical Report, Series 9, 10(1):41-46.
Sysmex "Action mechanism of leukocytes by special reagents for automated leukocyte differentiation (DIFF channel)" The Cell Analysis Center—Scientific Bulletin Part 5, 2008, XP055183570.
Sysmex XE-2100 Operator's Manual, Chapter 7, Functional Description, Revised Jul. 2007, XP55182265.
SYTO-Dyes, Invitrogen Nucleic Staining Dyes, Webpage, 2009.
SYTO-Dyes, Molecular Probes Handbook, Table 8.3, 2009.

WHITE BLOOD CELL ANALYSIS SYSTEM AND METHOD

CROSS REFERENCE TO RELATED APPLICATIONS

This application claims the benefit under 35 U.S.C. §119 (e) of U.S. Provisional Patent Application No. 61/482,541, titled, Method For Analyzing White Blood Cells, and filed on May 4, 2011, the entire disclosure of which is incorporated by reference herein.

This application is also related to application Ser. No. 13/456,738, filed on Apr. 26, 2012, titled "NUCLEATED RED BLOOD CELL ANALYSIS SYSTEM AND METHOD," and application Ser. No. 13/456,744, filed on Apr. 26, 2012, titled "BASOPHIL ANALYSIS SYSTEM AND METHOD," the entire disclosures of which are herein incorporated by reference in their entirety.

BACKGROUND

This invention relates to hematology systems and methods. More specifically, this invention relates to systems and methods for analyzing blood samples to identifying, classify, and/or quantify white blood cells (WBC) and WBC sub-populations in a sample of blood.

The development of an accurate and efficient hematology assay for analysis of WBCs, including counting and classification, has been a challenge. One reason for the difficulty in developing an accurate and efficient assay is the relatively low concentration of WBCs (approximately 0.1% to 0.2%) amongst total blood cells in a sample. Attempts to engineer advanced methods for analyzing WBCs, and formulating robust WBC reagent(s), have remained one of the top priorities in the area of automated hematology analyzers.

Typically, lysis of red blood cells (RBCs) is required to eliminate interference from RBCs, and concentrate WBCs, before counting and classifying WBCs and WBC sub-populations. More specifically, accurate and efficient WBC analysis requires: (1) complete lysis of RBCs in less than 30 seconds; (2) the breaking of large fragments of RBCs into smaller pieces after lysis; and (3) the preservation of WBCs for accurate counting and proper classification. If the blood sample is "under-lysed," unlysed RBCs, even in very small concentrations, interfere with WBC counting and differential analysis. Similarly, larger fragments of lysed RBCs can interfere with WBC counting and differential analysis. In practice, it is difficult to separate unlysed RBCs and/or larger fragments of lysed RBCs from lymphocytes (the smallest WBCs). If the blood sample is "over-lysed," the classification of WBCs may be adversely affected on account of excessive damage to cell membranes of WBCs.

In some instances, the difficulty of WBC analysis may be compounded by the presence of two special types of samples; namely, samples containing lysis-resistant red blood cells (rstRBCs) and samples containing fragile lymphocytes. In the case of samples containing rstRBCs, the WBC count and percentage of lymphocytes are falsely reported "high," on account of the contribution of particles other than true lymphocytes, consequently posing a risk of improper diagnoses and treatments for patients. In the case of samples containing fragile lymphocytes, damaged lymphocytes may not show their characteristics in a WBC differential analysis. In addition, exposed nuclei of WBCs may be counted as nucleated red blood cells (nRBCs), resulting in a false positive count of nRBCs in certain assays.

BRIEF SUMMARY

Provided herein are systems and methods for analyzing blood samples, and more specifically for performing a white blood cell (WBC) differential analysis. In general, the systems and methods disclosed screen WBCs by means of fluorescence staining and a fluorescence triggering strategy. As such, interference from unlysed RBCs (e.g., rstRBCs) and RBC fragments is substantially or completely eliminated, thereby ensuring accurate counting and differentiation of WBCs and WBC sub-populations. The systems and methods also enable development of relatively milder WBC reagent(s), suitable for assays of samples containing fragile lymphocytes (or other fragile WBCs), including aged samples.

In one embodiment, for example, the systems and methods disclosed herein include: (a) staining a blood sample with an exclusive, cell membrane permeable, fluorescent dye, which corresponds in emission spectrum to an excitation source of a hematology instrument; (b) using a fluorescence trigger to screen the blood sample for WBCs; and (c) using a combination of measurements of (1) axial light loss, (2) intermediate angle scatter, (3) 90° polarized side scatter, (4) 90° depolarized side scatter, and (5) fluorescence emission to perform a differential analysis.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

FIG. 1A is a histogram showing the measurement of an axial light loss signal.

FIG. 1B is a histogram showing the measurement of intermediate angle scatter.

FIG. 1C is a histogram showing the measurement of 90° polarized side scatter.

FIG. 1D is a histogram showing the measurement of 90° depolarized side scatter.

FIG. 1E is a histogram showing the measurement of fluorescence.

FIG. 5A is a cytogram depicting axial light loss vs. intermediate angle scatter.

FIG. 5B is a cytogram depicting 90° polarized side scatter vs. axial light loss.

FIG. 5C is a cytogram depicting 90° polarized side scatter vs. intermediate angle scatter.

FIG. 5D is a cytogram depicting 90° depolarized side scatter vs. axial light loss.

FIG. 5E is a cytogram depicting 90° depolarized side scatter vs. intermediate angle scatter.

FIG. 5F is a cytogram depicting 90° depolarized side scatter vs. 90° polarized side scatter.

FIG. 5G is a cytogram depicting fluorescence vs. axial light loss.

FIG. 5H is a cytogram depicting fluorescence vs. intermediate angle scatter.

FIG. 5I is a cytogram depicting fluorescence vs. 90° polarized side scatter.

FIG. 5J is a cytogram depicting fluorescence vs. 90° depolarized side scatter.

DETAILED DESCRIPTION

Figure 1A:
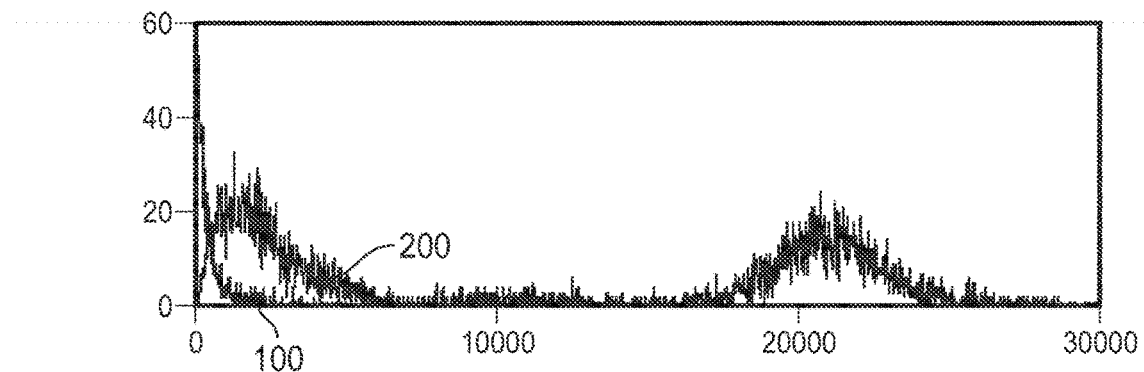
FIGS. 1A-1E show histograms of a sample of whole blood, showing WBCs and residues of RBCs following lysis.

Provided herein are systems and methods for analyzing blood samples, and more specifically for performing a white blood cell (WBC) differential analysis to identify, classify, and count WBCs and WBC sub-populations. In general, the systems and methods disclosed screen WBCs by means of fluorescence staining and a fluorescence triggering strategy. As such, interference from unlysed red blood cells (RBCs), such as lysis-resistant red blood cells (rstRBCs), and RBC fragments is substantially eliminated. The systems and methods disclosed thereby ensure accurate counting and differentiation of WBCs and WBC sub-populations. The systems and methods also enable development of relatively milder WBC reagent(s), suitable for assays of samples containing fragile lymphocytes (or other fragile WBCs), including aged samples.

In one embodiment, for example, the systems and methods disclosed herein include: (a) staining a blood sample with an exclusive, cell membrane permeable, fluorescent dye, which corresponds in emission spectrum to an excitation source of a hematology instrument; (b) using a fluorescence trigger to screen the blood sample for WBCs; and (c) using a combination of measurements of (1) axial light loss, (2) intermediate angle scatter, (3) 90° polarized side scatter, (4) 90° depolarized side scatter, and (5) fluorescence emission to perform a WBC differential analysis.

As used herein, the expression "fluorescence information" means data collected from a fluorescence channel of a hematology analyzer. As used herein, the expression "fluorescence channel" means a detection device, such as a photomultiplier tube, set at an appropriate wavelength band for measuring the quantity of fluorescence emitted from a sample.

(1) Use of Fluorescent Dye(s).

WBCs contain a relatively high concentration of DNA in their nuclei. Mature RBCs, however, do not contain DNA. Therefore, a fluorescent dye is selected to differentiate two classes of blood cells; namely, the blood cells containing nucleic acids and the blood cells not containing nucleic acids. The purpose of the dye is to penetrate into live cells easily, bind DNA with high affinity, and emit strong fluorescence with adequate Stokes shift when the dye is excited by an appropriate source of light. The peak absorption of the dye in the visible band substantially matches the wavelength of the source of light (within 50 nm of the wavelength of the source of light, more preferably, within 25 nm of the wavelength of the source of light), in order to be properly excite the dye and achieve optimal results.

The fluorescent dye selected is preferably: 1) capable of binding nucleic acids, 2) capable of penetrating cell membranes of WBCs, 3) excitable at a selected wavelength when subjected to a source of light, 4) emits fluorescence upon excitation by the source of light, and 5) is biostable and soluble in a liquid. The dye may be selected from group consisting of: acridine orange, SYBR 11, SYBR Green series dye, hexidium iodide, SYTO 11, SYTO 12, SYTO 13, SYTO 14, SYTO 16, SYTO 21, SYTO RNA Select, SYTO 24, SYTO 25 and any equivalents thereof. The dye is used to "activate" WBCs and "screen out" unlysed RBCs and fragments of RBCs based on a fluorescence trigger configured in the hematology analyzer. The dye is typically present at a concentration of from about 0.1 ng/mL to about 0.1 mg/mL. While various dyes are available, the dye selected is generally paired with the excitation source of the hematology analyzer such that a single exclusive dye is used to stain and excite fluorescence emission in all WBC subpopulations intended to be identified, quantified, and/or analyzed. As such, a single (i.e., exclusive) dye can be used to identify, quantify, and analyze all the WBC subpopulations at once.

In one embodiment, a fluorescent dye is provided in a WBC reagent, with combinations of 1) at least one surfactant, 2) at least one buffer, 3) at least one salt, and/or 4) at least antimicrobial agent, in sufficient quantities for carrying out staining and activating up to $1,000 \times 10^3$ WBCs per microliter. The at least one surfactant, such as "TRITON" X-100 or saponin, is used to destroy the membranes of RBC, and reduce the sizes of fragments of RBCs. The at least one surfactant is typically present at a concentration of from about 0.001% to about 5%. The at least one antimicrobial agent, such as those from "TRIADINE" or "PROCLIN" families, is used to prevent the contamination of the reagent from microbes. The concentration of the at least one antimicrobial agent is sufficient to preserve the reagent for the shelf life required. The at least one buffer, such as phosphate buffered saline (PBS) or 4-(2-hydroxyethyl)-1-piperazineethanesulfonic acid (HEPES), is used to adjust the pH of reaction mixture for controlling lysis of RBCs and preserving WBCs. The at least one buffer is typically present at a concentration of from about 0.01% to about 3%. The pH typically ranges from about 3 to about 12. The at least one salt, such as NaCl or $Na_2SO_4$, is used to adjust the osmolality to increase the effect of lysing and/or optimize WBC preservation. The at least one salt may be present at a concentration of from about 0.01% to about 3%. In certain cases, the at least one buffer can serve as the at least one salt, or the at least one salt can serve as the at least one buffer. In general, lower osmolality, or hypotonicity, is used to accelerate the lysis of RBCs. The osmolality typically ranges from about 20 to about 250 mOsm.

Lysis of RBCs can be made to occur at a temperature above room temperature (e.g., between about 30° C. to about 50° C., such as about 40° C.) over a relatively short period of time (e.g., less than about 25 seconds, less than about 17 seconds, or even less than about 9 seconds), following mixing of the sample of blood and the WBC reagent at a ratio of about one part by volume sample to about 35 parts by volume WBC reagent. The data for analysis is collected with a plurality of optical channels and at least one fluorescence channel.

Figure 1B:
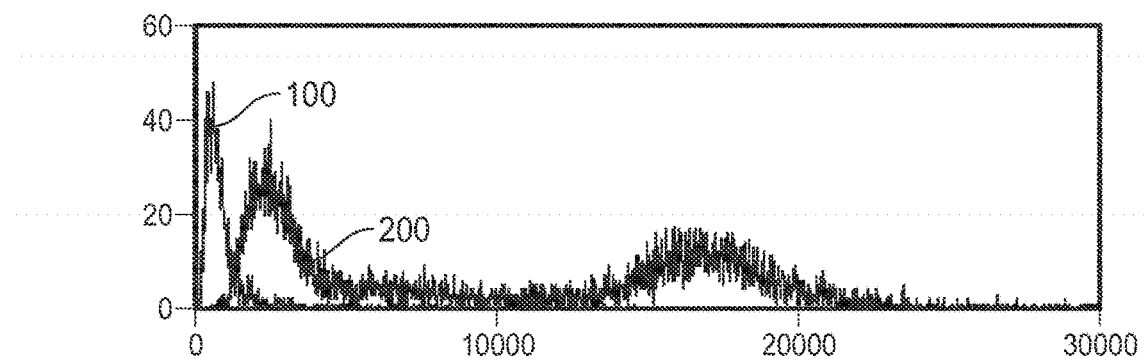
Figure 1C:
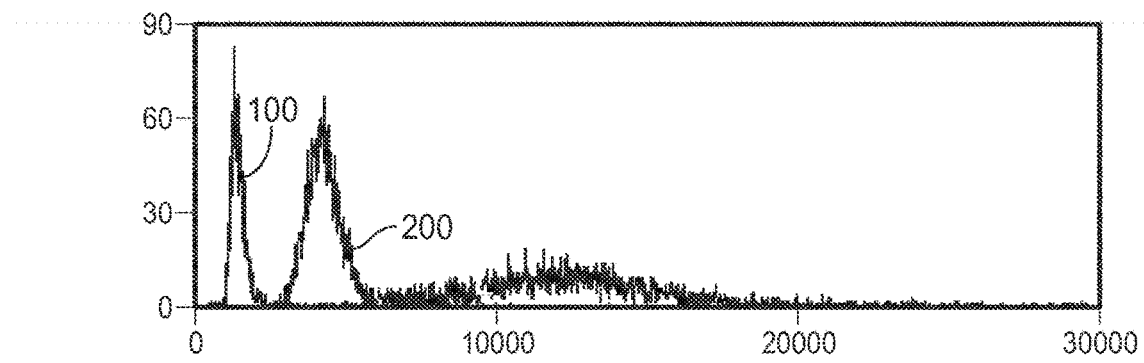
Figure 1D:
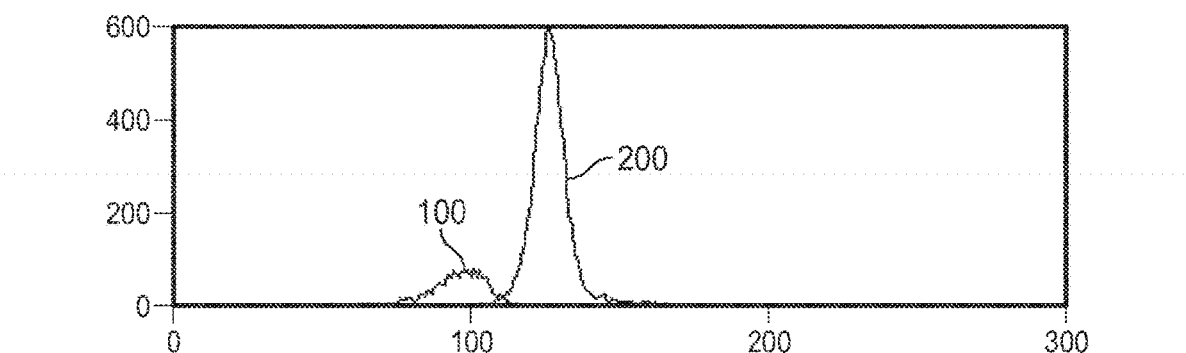
Figure 1E:
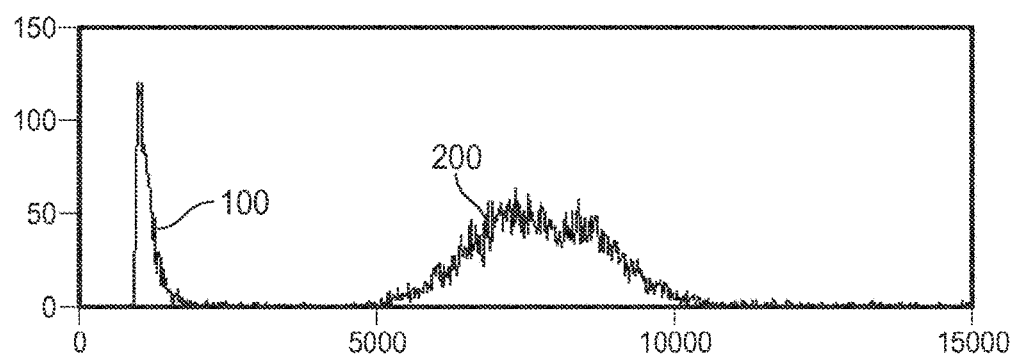

FIGS. 1A-E show the separation of true WBCs from unlysed RBCs and RBC fragments, in histograms of collected optical information and a histogram of fluorescence information. The histogram in FIG. 1A shows a measurement of axial light loss (ALL). The histogram in FIG. 1B shows a measurement of intermediate angle scatter (IAS). The histogram in FIG. 1C shows a measurement of 90° polarized side scatter (PSS). The histogram in FIG. 1D shows a measurement of 90° depolarized side scatter (DSS). The histogram in FIG. 1E shows a measurement of fluorescence (FL1). In the histograms, the horizontal axis indicates the value of the detection channel (or the names of the channels, i.e., ALL, IAS, PSS, DSS or FL1). The vertical axis indicates counts of components of the sample of blood. In the histograms, the lines 100 indicate residues of RBCs and lines 200 indicate WBCs. As used herein, "residues of RBCs" is synonymous with "fragments of RBCs." As shown by comparing FIG. 1E to FIGS. 1A-1D, fluorescence information shows much better separation between the two groups of particles (i.e., WBCs and residues of RBCs) than do any of the optical channels, thereby facilitating the following analysis.

(2) Use of a Fluorescence Trigger.

Blood cells emit different magnitudes of fluorescence signals upon excitation of the fluorescent dye by a source of light. The differences in magnitude of fluorescence signals arise from the quantity of nucleic acids, namely DNA, inside the cells. The greater the quantity of DNA, the greater the likelihood of higher fluorescence signals. Also, efficacy of penetration of cell membranes, size of the dye, binding kinetics between the dye and DNA, affinity between the dye and DNA, and other factors, affect the fluorescence signals. Mature RBCs emit minimal fluorescence signals because there is no DNA within mature RBCs. Nucleated red blood cells (nRBCs) emit very strong fluorescence signals, because not only is DNA inside nuclei of nRBCs, but also the staining is easier because membranes of nRBCs are destroyed during the lysis procedure. Unlysed RBCs or RBC fragments do not emit fluorescence, although they may emit very weak auto-fluorescence. As shown with reference to FIG. 1E, the cells that emit much stronger fluorescence signals are the cells having nuclei, namely, WBCs (and nRBCs when present).

Figure 2:
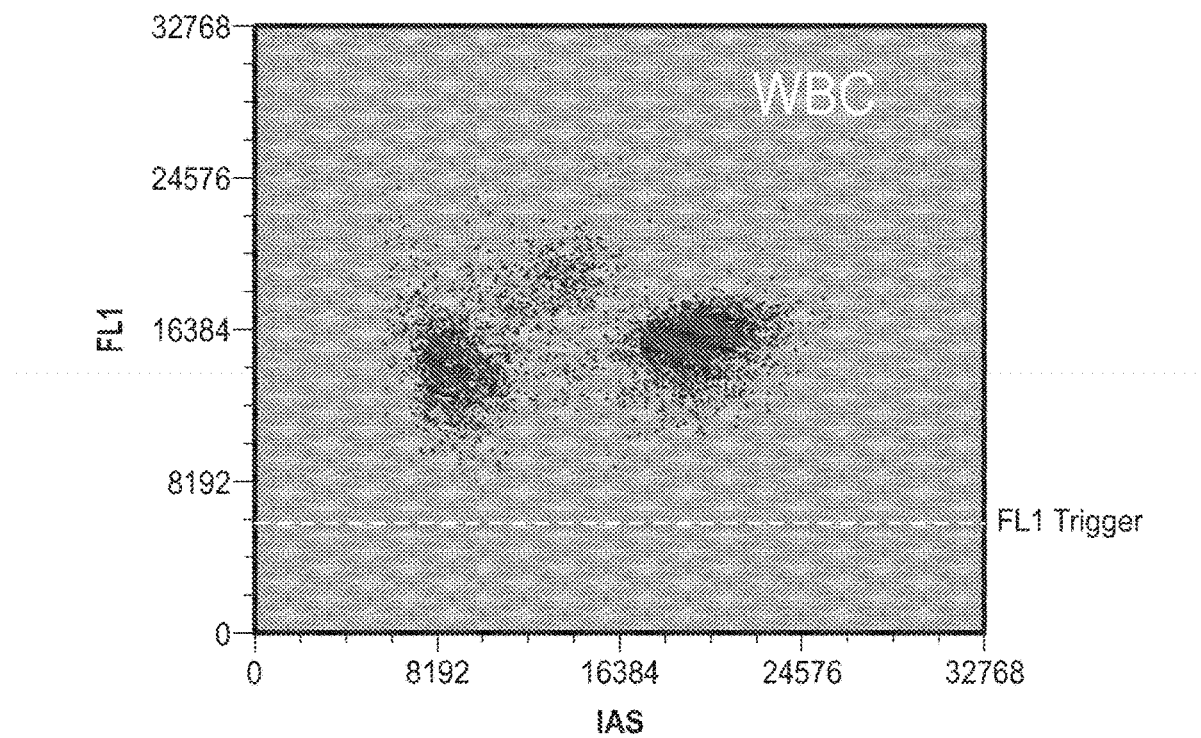
FIG. 2 is a cytogram showing the use of a fluorescent trigger for eliminating any fragments of RBCs from consideration.
Figure 3:
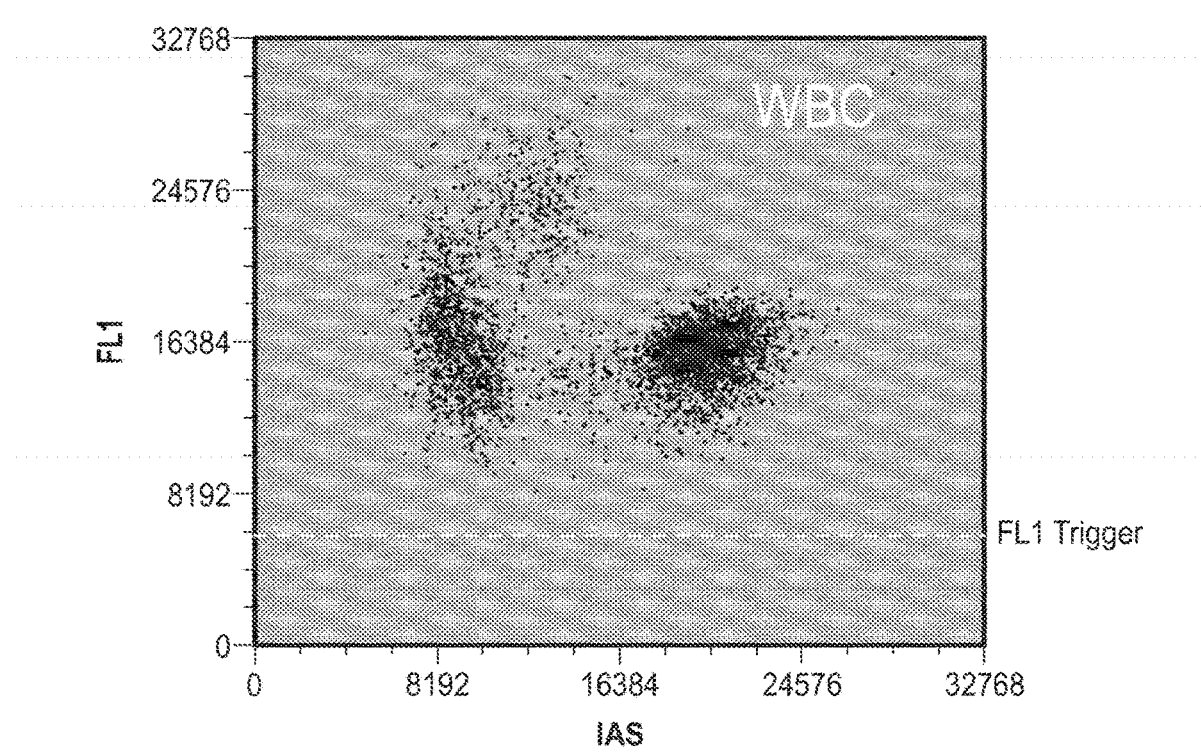
FIG. 3 is another cytogram showing the use of a fluorescent trigger for eliminating any fragments of RBCs from consideration.

As such, the systems and methods presented herein use a fluorescence trigger for collecting and analyzing WBCs. For example, a fluorescence trigger, usually set between signals from RBCs and signals from WBCs, can be used to collect signals from WBCs separately for further analysis. Two examples of using an FL1 trigger are shown in FIG. 2 and FIG. 3. FIG. 2 is a cytogram showing the use of a fluorescent trigger for eliminating any fragments of RBCs (nuclei-free particles) and collecting nuclei-containing events (e.g., WBCs and/or nRBCs). The fluorescent dye was acridine orange and the concentration of the fluorescent dye was 3 μg/mL. The voltage of the fluorescent photomultiplier tube was set at 350 volts. FIG. 3 is a cytogram showing the use of a fluorescent trigger for eliminating any fragments of RBCs (nuclei-free particles) and collecting nuclei-containing events (e.g., WBCs and/or nRBCs). The fluorescent dye was acridine orange and the concentration of the fluorescent dye was 0.03 μg/mL. The voltage of the fluorescent photomultiplier tube was set at 500 volts. In a WBC assay using acridine orange staining (even with drastically different concentrations of the dyes, i.e., 3 μg/mL in FIG. 2 and 0.03 μg/mL in FIG. 3) and a properly set FL1 trigger, only the events above the FL1 trigger are nuclei-containing events (e.g., WBCs and/or nRBCs, if present) and, consequently, are captured for further analysis.

(3) Use of a Plurality of Optical Channels and at Least One Fluorescence Channel for Analysis.

In one embodiment, the WBC differential analysis is conducted by means of Multiple Angle Polarized Scattering Separation technology (MAPSS), with enhancement from fluorescence information. At least one photodiode, or at least one photomultiplier tube, or both at least one photodiode and at least one photomultiplier tube, are needed to detect light scattered by each blood cell passing through a flow cell. Two or more photodiodes are used for measuring ALL signals, which measure about 0° scatter, and IAS signals, which measure low angle (e.g., about 3° to about 15°) scatter. Two or more photomultiplier tubes are used for detecting 90° PSS signals and 90° DSS signals. Additional photomultiplier tubes are needed for FL1 measurements within appropriate wavelength range(s), depending on the choice of wavelength of the source of light. Each event captured on the system thus exhibits a plurality of dimensions of information, such as ALL, IAS (one or more channels), PSS, DSS, and fluorescence (one or more channels). The information from these detection channels is used for further analysis of blood cells.

Figure 4:
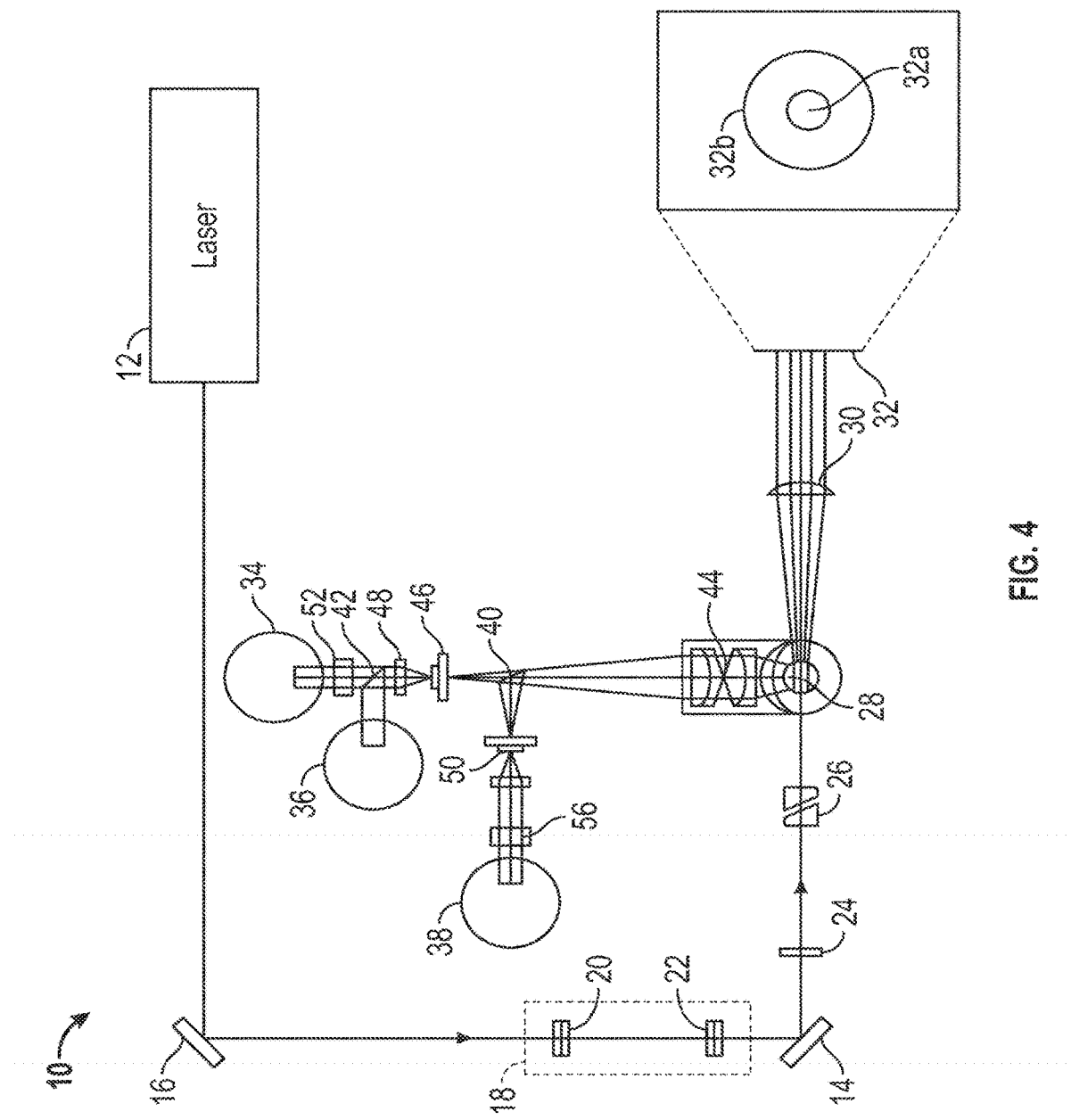
FIG. 4 is a schematic diagram illustrating a hematology instrument.

FIG. 4 is a schematic diagram illustrating the illumination and detection optics of an apparatus suitable for hematology analysis (including flow cytometry). Referring now to FIG. 4, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In the discussion that follows, the source of light is preferably a laser. However, other sources of light can be used, such as, for example, lamps (e.g., mercury, xenon). The source of light 12 can be a vertically polarized air-cooled Coherent Cube laser, commercially available from Coherent, Inc., Santa Clara, Calif. Lasers having wavelengths ranging from 350 nm to 700 nm can be used. Operating conditions for the laser are substantially similar to those of lasers currently used with "CELL-DYN" automated hematology analyzers.

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The forward optical path system shown in FIG. 4 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS). The second photomultiplier tube 36 (PMT2) measures polarized side scatter (PSS), and the third photomultiplier tube 38 (PMTS) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 4, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include bandpass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

While select portions of U.S. Pat. No. 5,631,165 are referenced above, U.S. Pat. No. 5,631,165 is incorporated herein by reference in its entirety.

Figure 5A:
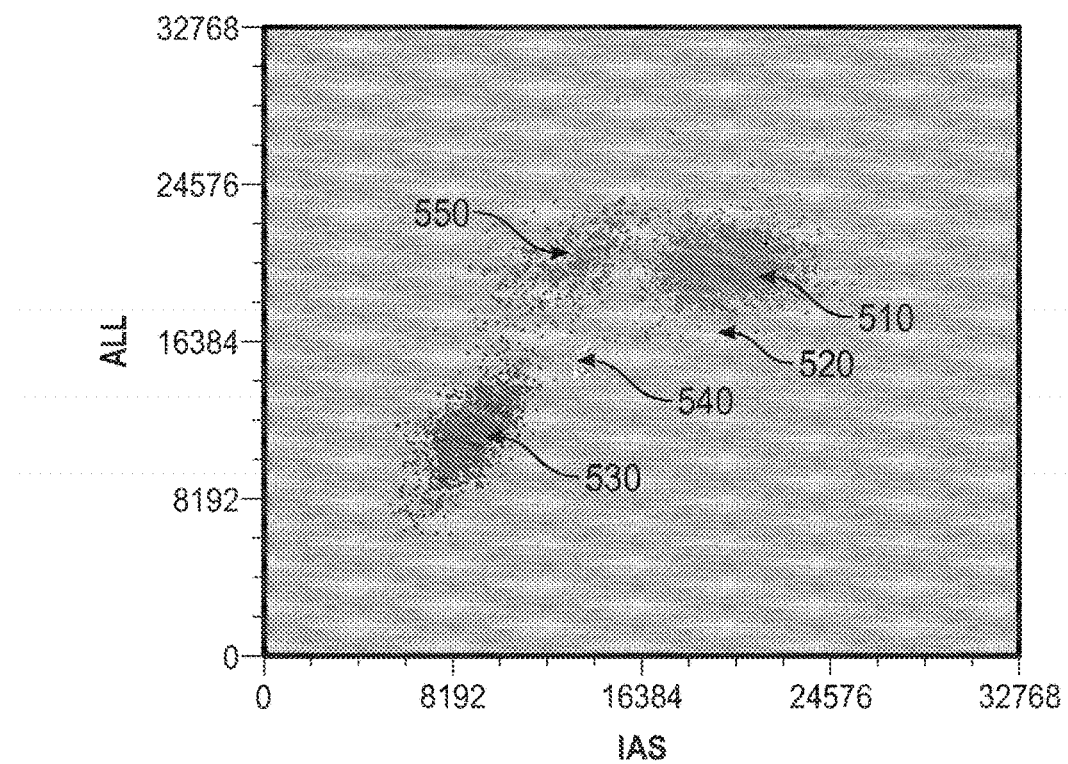
FIGS. 5A-5J show cytograms of a five-part WBC differential analysis.
Figure 5B:
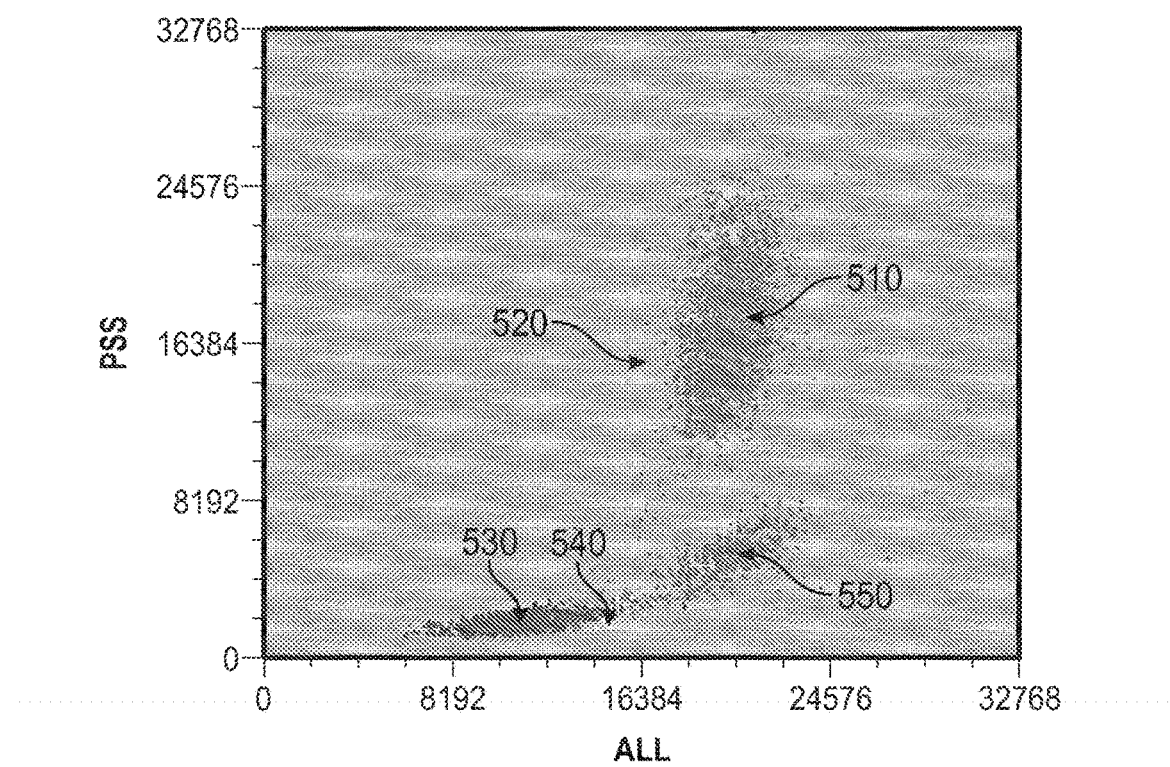
Figure 5C:
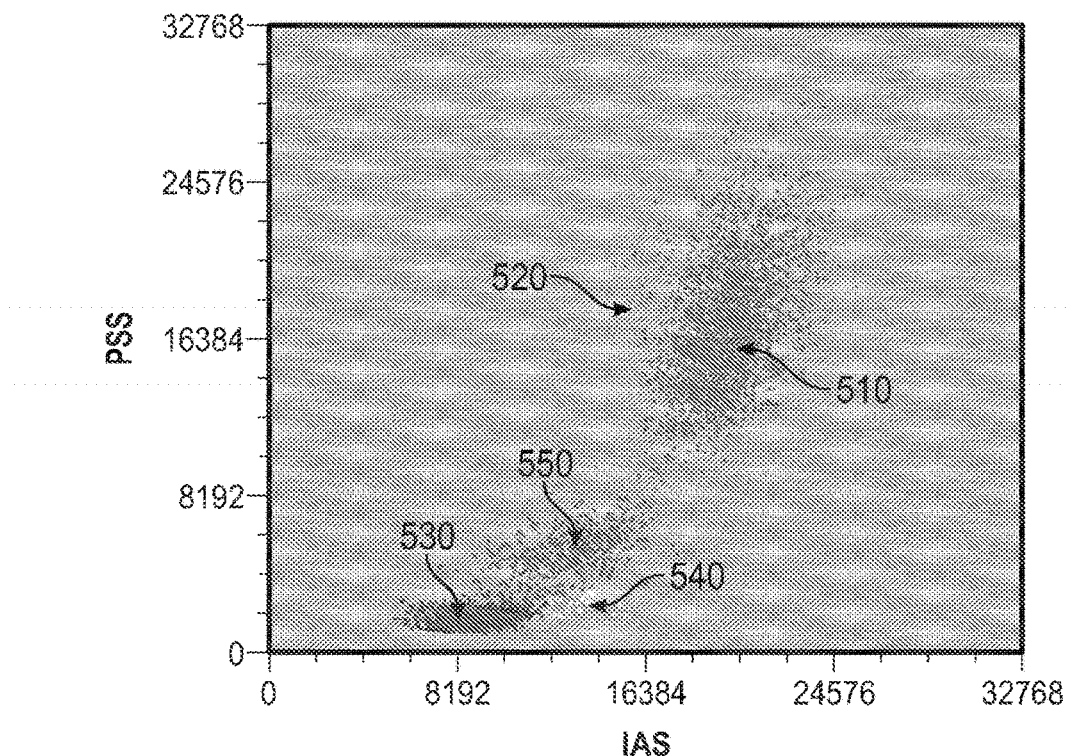
Figure 5D:
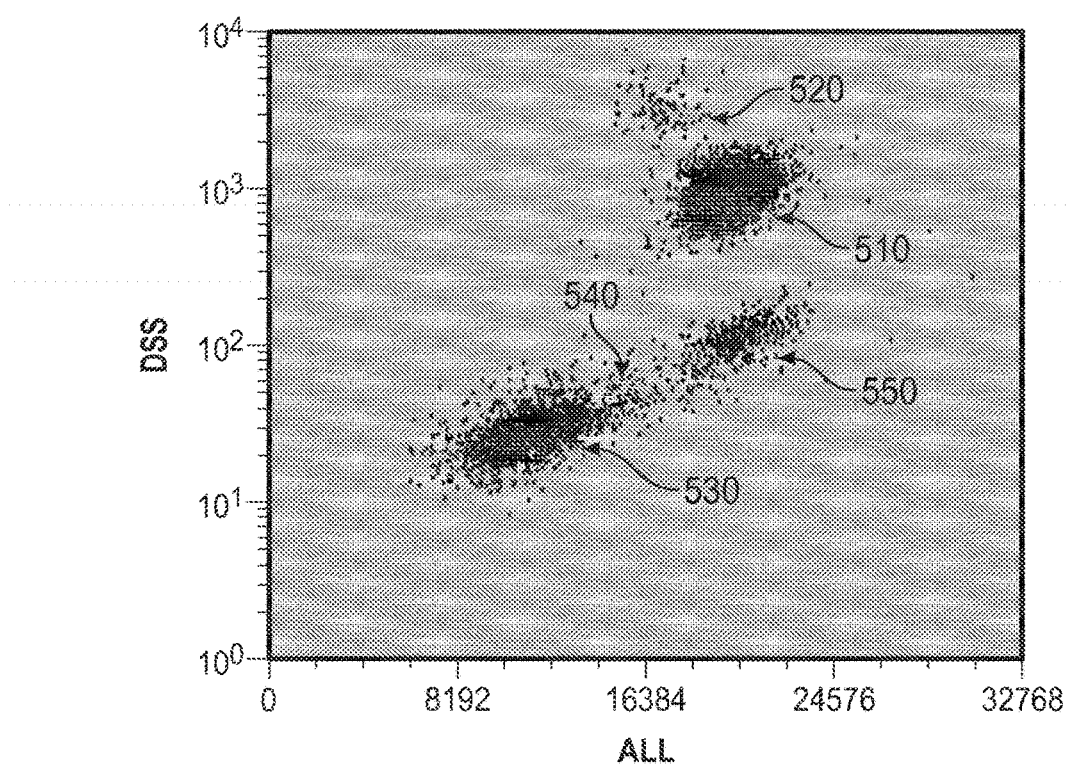
Figure 5E:
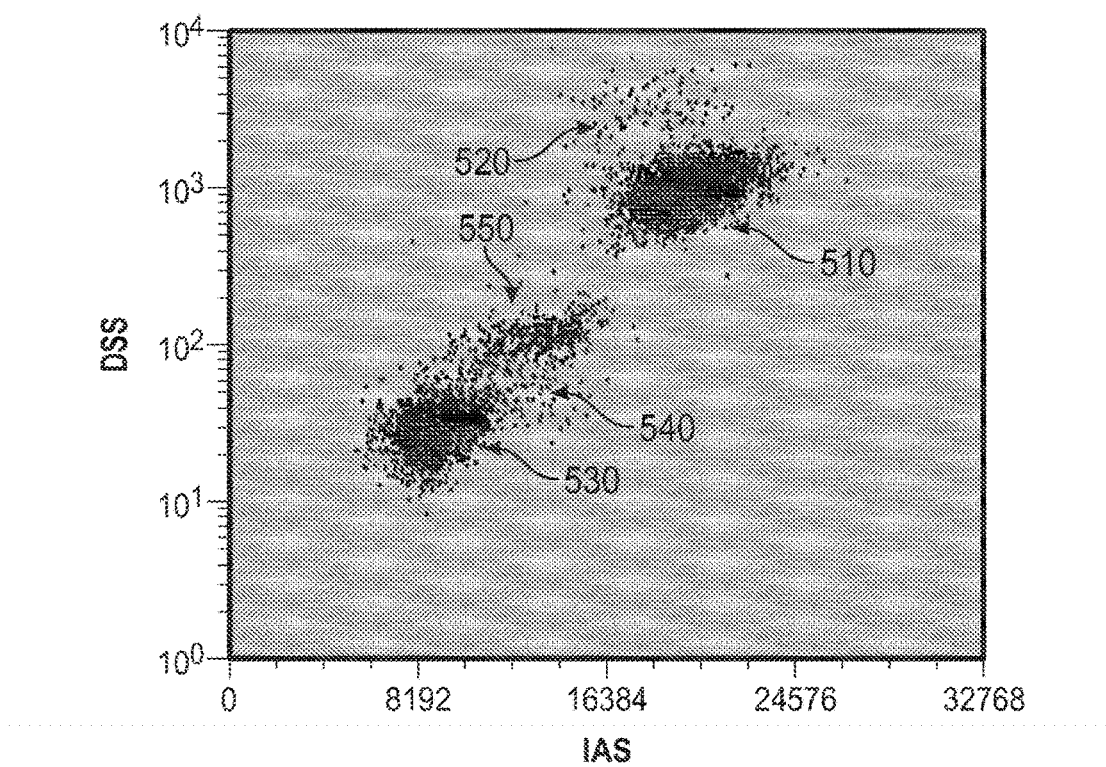
Figure 5F:
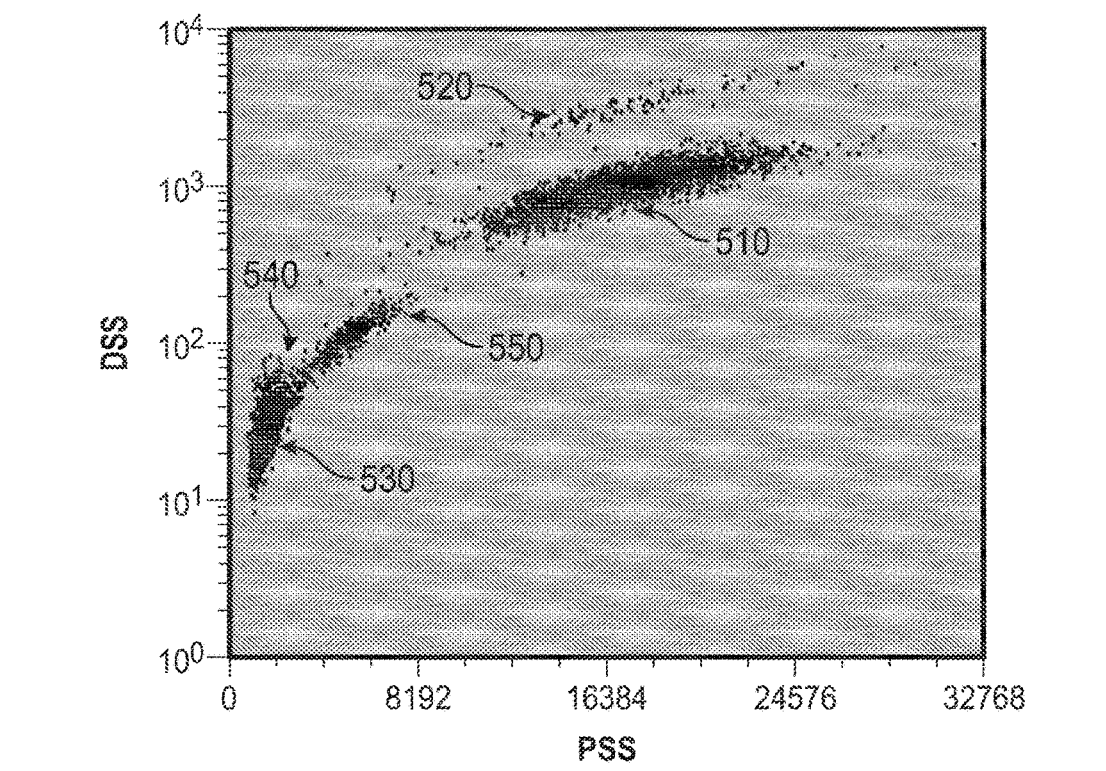
Figure 5G:
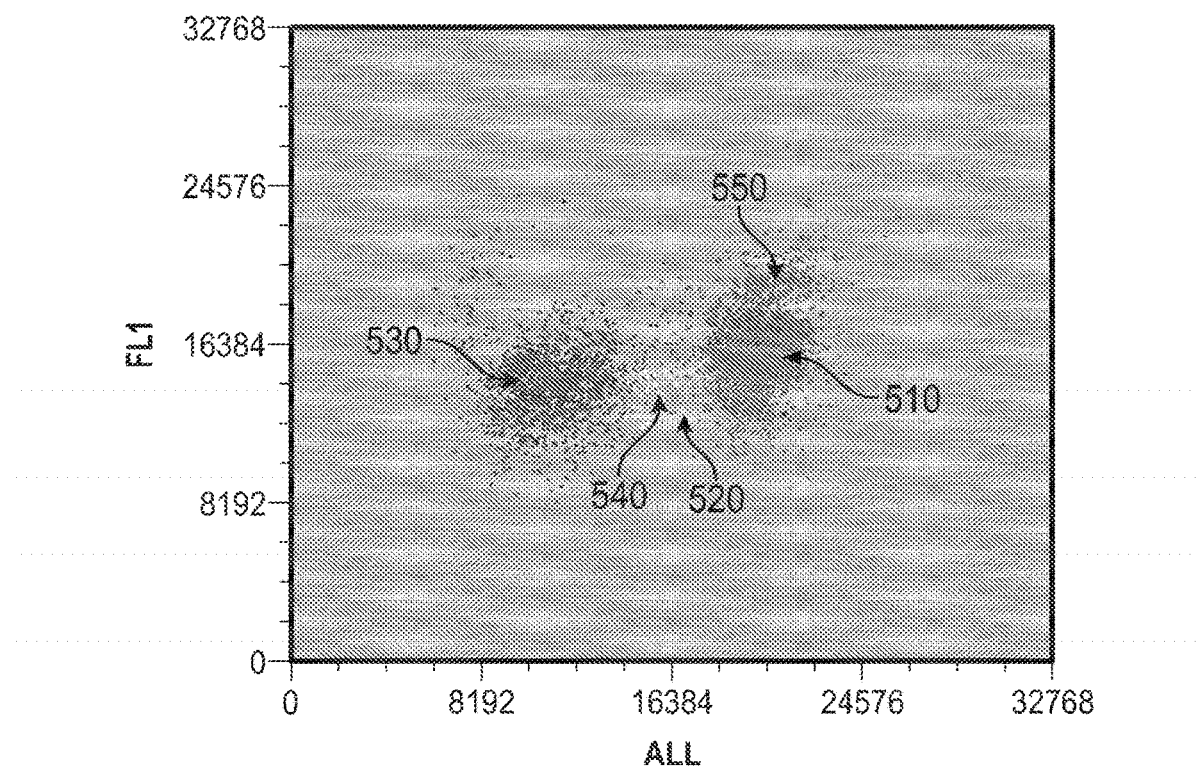
Figure 5H:
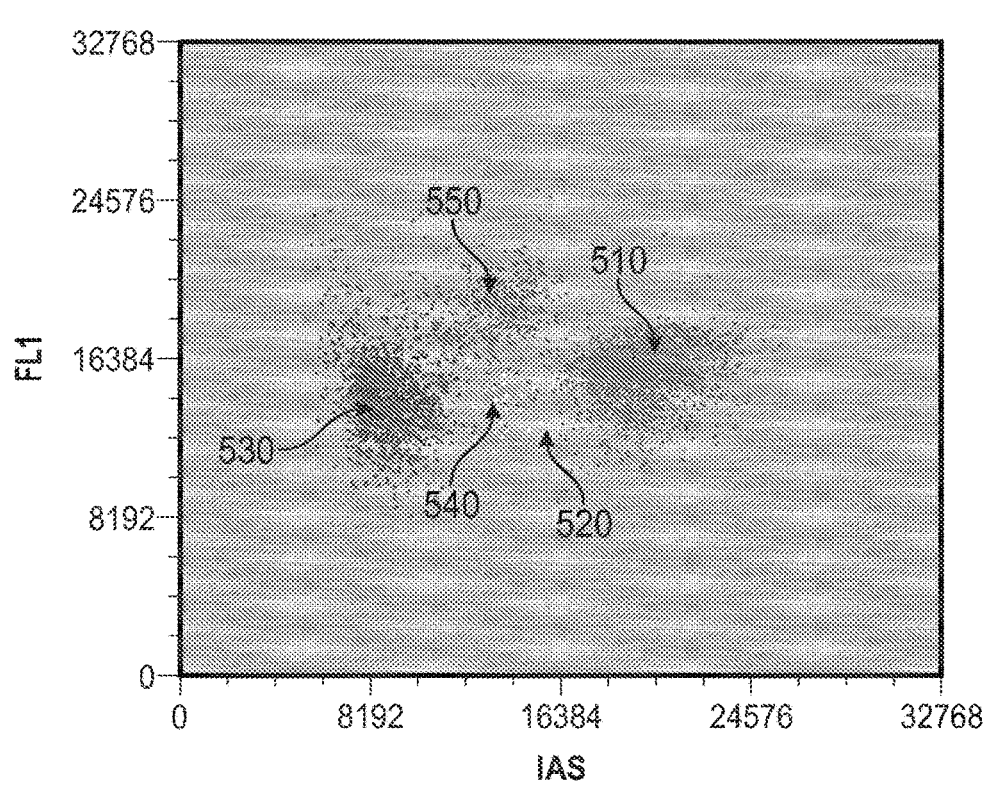
Figure 5I:
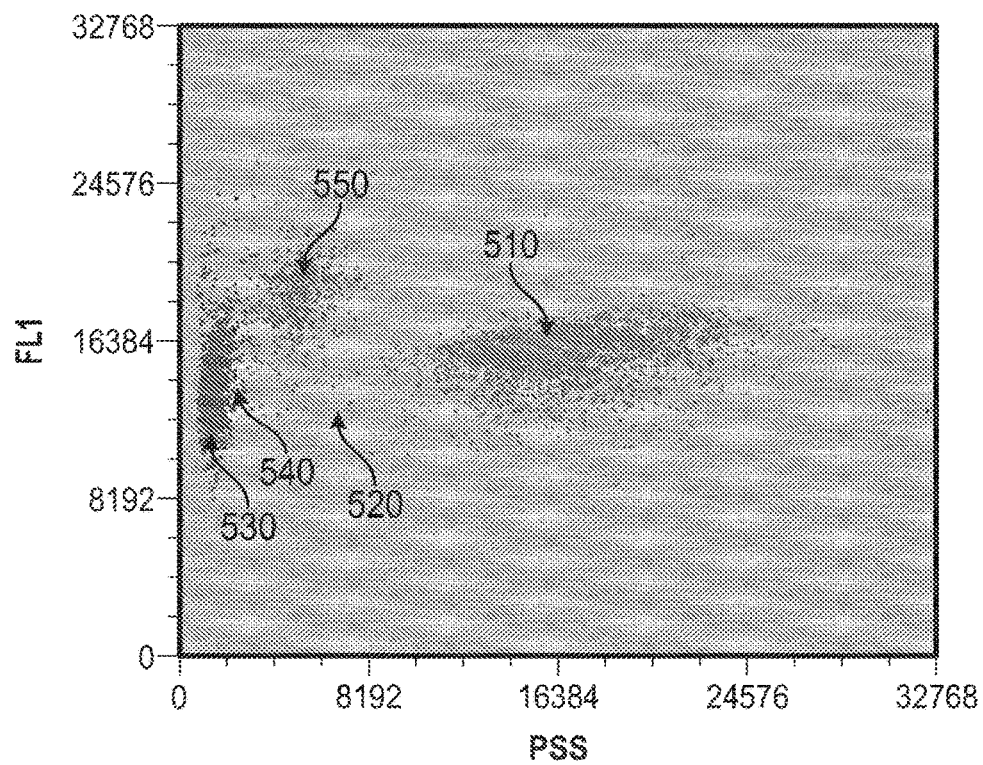
Figure 5J:
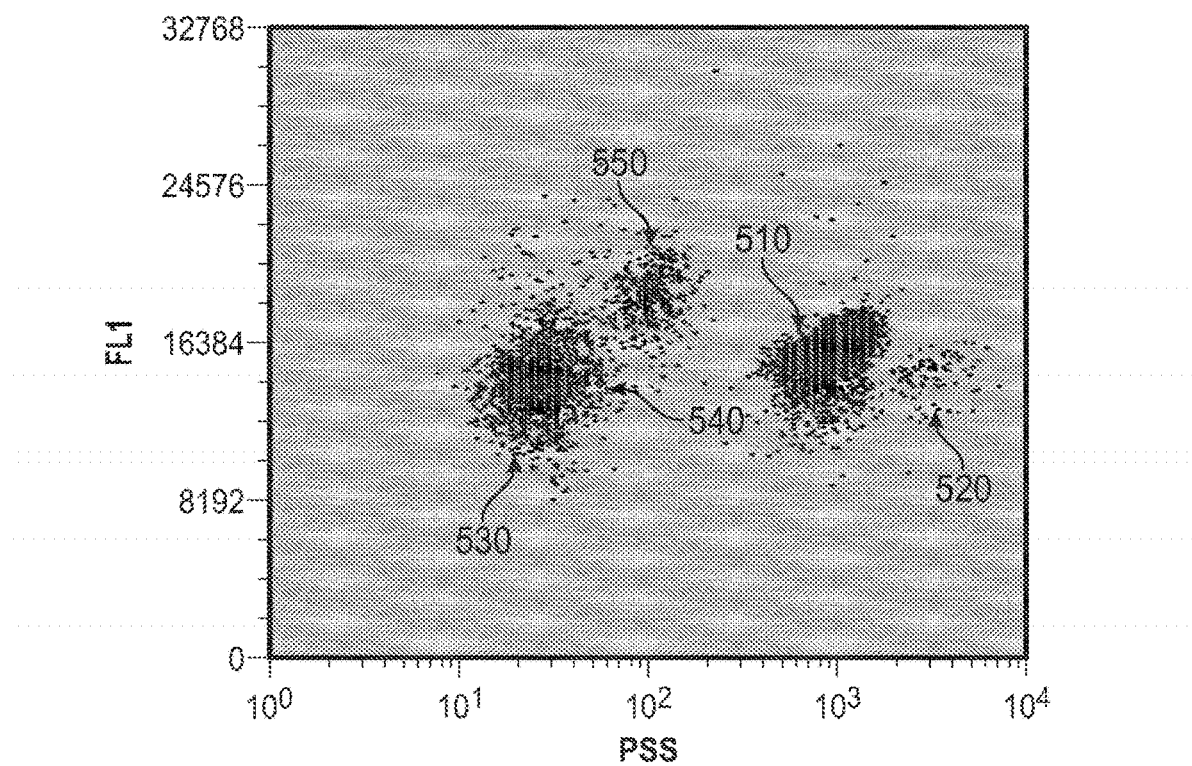

FIGS. 5A-J show an example of an enhanced five-part WBC differential analysis. Neutrophils (NE), lymphocytes (LY), monocytes (MO), eosinophils (EO) and basophils (BA) were separated using MAPSS technology and a FL1 channel. The cytogram in FIG. 5A shows ALL vs. IAS. The cytogram in FIG. 5B shows 90° PSS vs. ALL. The cytogram in FIG. 5C shows 90° PSS vs. IAS. The cytogram in FIG. 5D shows 90° DSS vs. ALL. The cytogram in FIG. 5E shows 90° DSS vs. IAS. The cytogram in FIG. 5F shows 90° DSS vs. 90° PSS. The cytogram in FIG. 5G shows FL1 vs. ALL. The cytogram in FIG. 5H shows FL1 vs. IAS. The cytogram in FIG. 5I shows FL1 vs. 90° PSS. The cytogram in FIG. 5J shows FL1 vs. 90° DSS.

In addition to the information collected from the four traditional MAPSS channels (ALL, IAS, PSS, DSS), the FL1 channel further distinguishes the cell sub-populations (FIGS. 5G through 5J, inclusive). For the case in which acridine orange is used as the dye for screening WBCs, basophils show relatively low FL1 signals, and monocytes show relatively high FL1 signals, relative to other WBC sub-populations, i.e., neutrophils, eosinophils, and lymphocytes. In the cytograms, dots 510 represent neutrophils, dots 520 represent eosinophils, dots 530 represent lymphocytes, dots 540 represent basophils, and dots 550 represent monocytes. The combined quantitative information from all optical dimensions and the fluorescence dimension provides an enhanced, and more reliable, differential analysis for samples of blood containing WBCs.

Figure 6A:
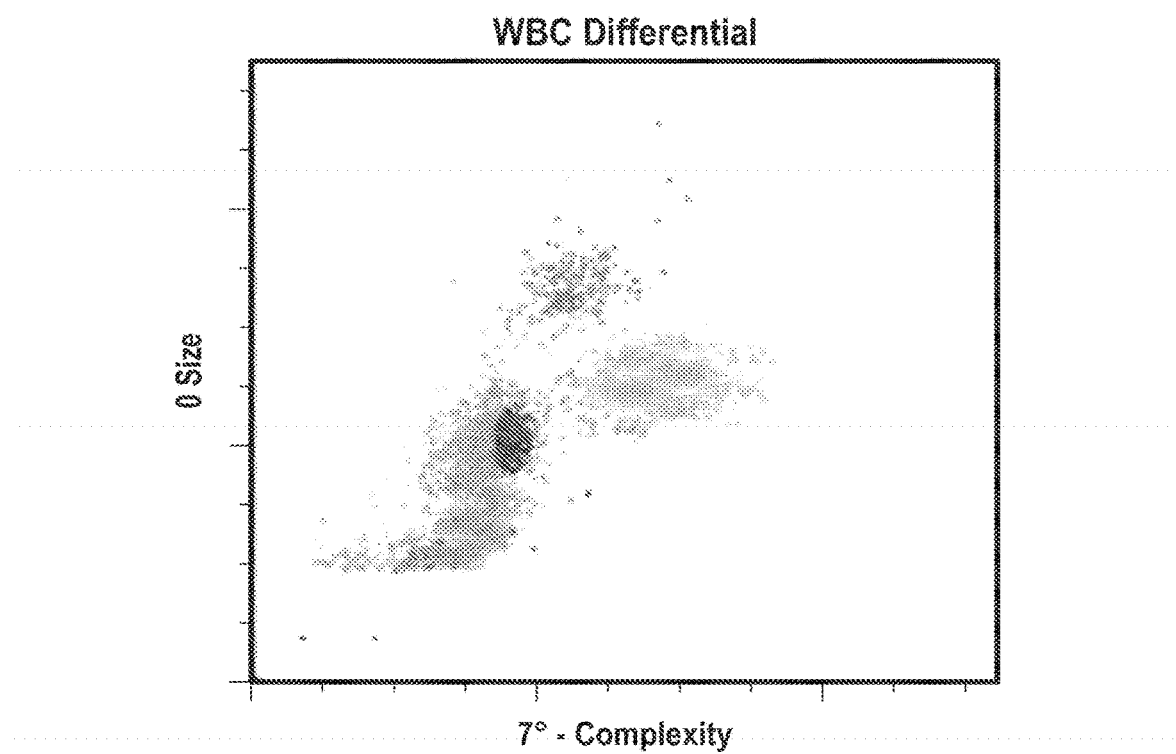
FIG. 6A is a cytogram illustrating analysis of a sample of whole blood containing lyse-resistant RBCs, using a traditional method.
Figure 6B:
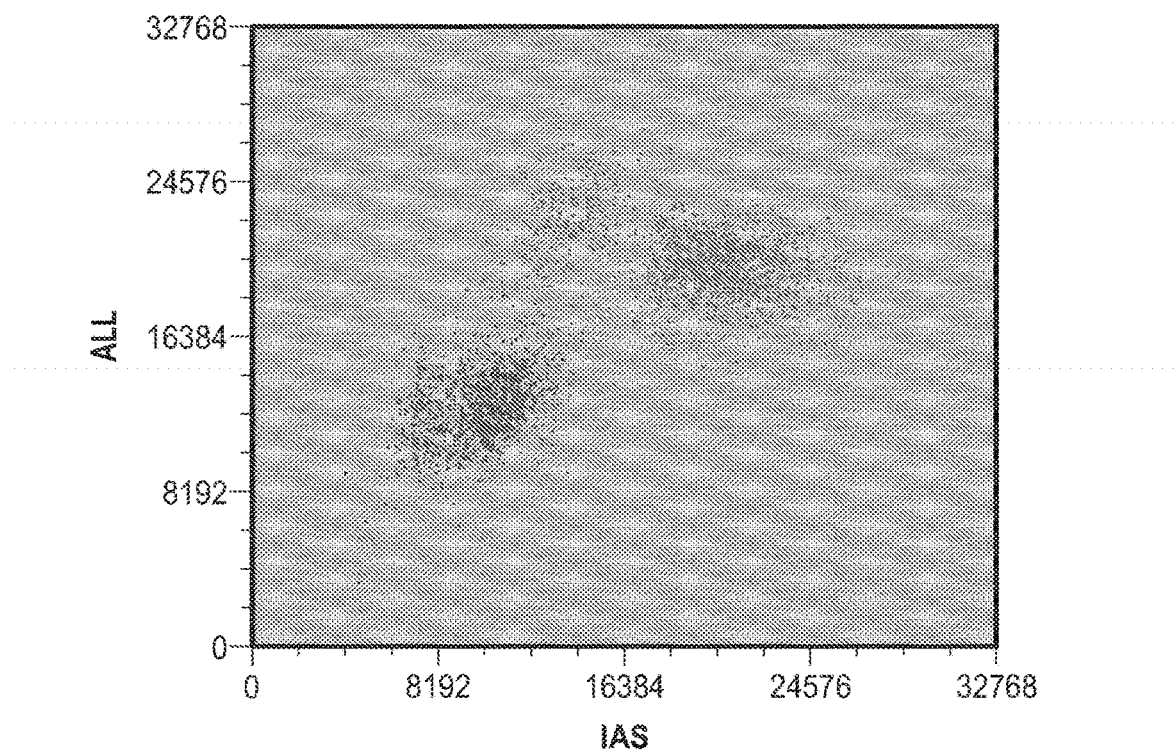
FIG. 6B is a cytogram showing axial light loss vs. intermediate angle scatter made by a fluorescence-triggered hematology analyzer, in accordance with an embodiment presented.

FIG. 6A is a cytogram illustrating analysis of a sample of whole blood containing rstRBCs, using a traditional method. FIG. 6A shows a cytogram of ALL vs. IAS, using a commercially available "CELL-DYN" Sapphire™ hematology analyzer. FIG. 6B is a cytogram showing ALL vs. IAS, using an FL1 trigger-enhanced hematology analyzer. The sample of whole blood was the same as that analyzed in FIG. 6A. The concentration of the fluorescent dye, acridine orange, was 3 µg/mL. The results show that the method described herein is accurate and efficient for the two most challenging cases mentioned previously. In the traditional method, unlysed RBCs, i.e., the events appearing in the lower left of the cytogram, were recognized as lymphocytes, thereby resulting in a higher count of WBCs and a higher percentage of lymphocytes. FIG. 6B shows the results of an analysis of WBCs of the sample containing rstRBCs by the method described herein. In the method described herein, the analysis of WBCs was accurate because no RBCs or residues of RBCs were recognized.

Figure 7A:
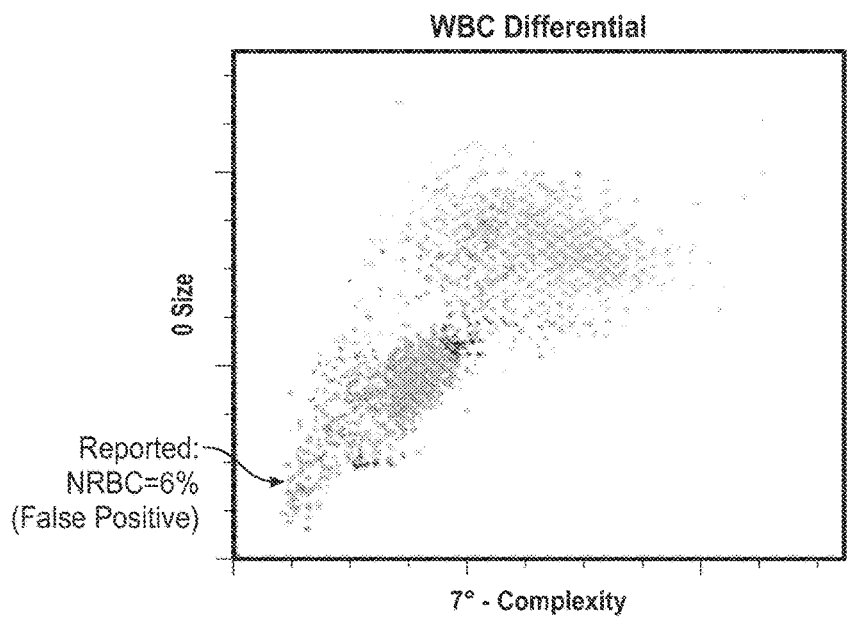
FIG. 7A is a cytogram illustrating analysis of an aged sample of whole blood, using a traditional method.
Figure 7B:
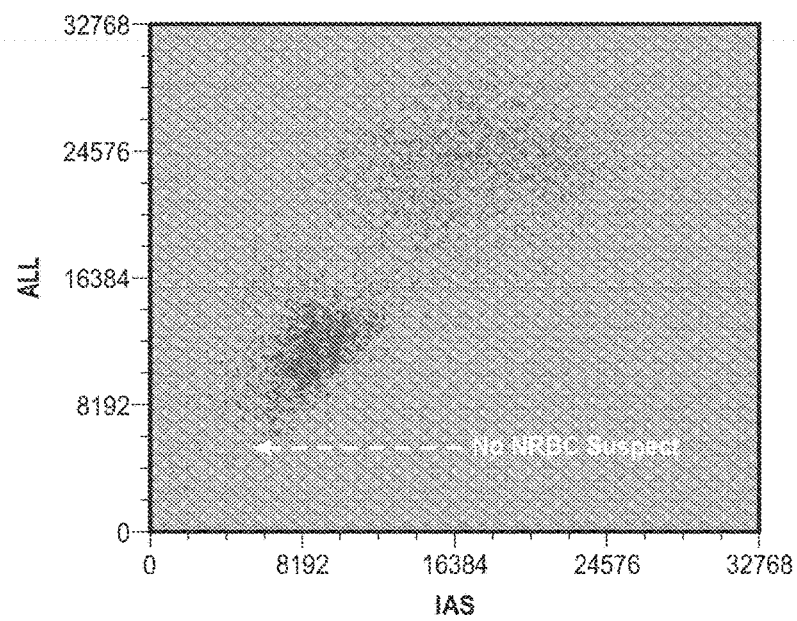
FIG. 7B is a cytogram showing axial light loss vs. intermediate angle scatter made by a fluorescence-triggered fluorescence-triggered hematology analyzer, in accordance with an embodiment presented.

FIG. 7A is a cytogram illustrating analysis of an aged (28 hours old) sample of whole blood, which contains more fragile WBCs, using a traditional method. FIG. 7A is a cytogram showing ALL vs. IAS, using a "CELL-DYN" Sapphire™ hematology analyzer. FIG. 7B is a cytogram showing ALL vs. IAS, using an FL1 trigger-enhanced hematology analyzer. The sample of whole blood was the same as that analyzed in FIG. 7A. The concentration of the fluorescent dye, acridine orange, was 3 µg/mL.

The methods described herein enhances WBC analysis for hematology analyzers.

The methods described herein provides a more accurate WBC count and a more accurate classification of WBC sub-populations, because the interference from unlysed RBCs and RBC fragments is substantially eliminated. The use of fluorescence provides further information to improve differential analysis of WBCs. The methods described herein shows advantages over traditional methods when analyzing samples having rstRBCs and samples having fragile WBCs.

Additional Embodiments

In one embodiment, there is provided a hematology analyzer for conducting a WBC differential analysis on a blood sample that has been dyed with a fluorescent dye. The analyzer comprises an excitation source positioned to excite particles within the blood sample. The analyzer further comprises a plurality of detectors including: (1) an axial light loss detector positioned to measure axial light loss from the excited blood sample, (2) an intermediate angle scatter detector positioned to measure intermediate angle scatter from the excited blood sample, (3) a polarized side scatter detector positioned to measure 90° polarized side scatter from the excited blood sample, (4) a depolarized side scatter detector positioned to measure 90° depolarized side scatter from the excited blood sample, and (5) a fluorescence detector positioned to measure fluorescence emitted from the excited blood sample. The analyzer further comprises a processor configured to receive the measurements of (1) axial light loss, (2) intermediate angle scatter, (3) 90° polarized side scatter, (4) 90° depolarized side scatter, and (5) fluorescence from the plurality of detectors. The processor is also configured to perform a WBC differential analysis of the blood sample, based on all five measurements, for particles that emit fluorescence above a fluorescence threshold. The processor may be further configured to pre-screen the received measurements to remove from consideration any particles that do not meet the fluorescence threshold. The axial light loss detector may measure axial light loss at 0° scatter. The intermediate angle scatter detector may measure light angle scatter at about 3° to about 15°. The plurality of detectors may include one or more photomultiplier tubes. The excitation source may be a laser configured to emit light at a wavelength corresponding to the fluorescent dye. Alternatively, the fluorescent dye may be selected to correspond with the excitation source. The fluorescent dye may be cell membrane permeable, and nucleic acid binding.

The hematology analyzer may further comprise an incubation subsystem for diluting the blood sample with a WBC reagent. The WBC reagent may include the fluorescent dye and one or more lysing agents. Alternatively, the WBC reagent may include (a) at least one surfactant, (b) at least one buffer or at least one salt, (c) at least one antimicrobial agent, and (d) the fluorescent dye. The incubation subsystem may be configured to incubate the blood sample with the WBC reagent for a period of time of less than about 25 seconds, less than about 17 seconds, or less than about 9 seconds. The incubation subsystem may also be configured to incubate the blood sample with the WBC reagent at a temperature ranging from about 30° C. to about 50° C., such as about 40° C.

In another embodiment, there is provided a method of configuring a hematology analyzer to perform a WBC differential analysis on a blood sample that has been dyed with a fluorescent dye. The method includes positioning an excitation source to excite particles within the blood sample. The method further includes positioning a plurality of detectors to measure (1) axial light loss, (2) intermediate angle scatter, (3) 90° polarized side scatter, (4) 90° depolarized side scatter, and (5) fluorescence from the excited blood sample. The method further comprises configuring a processor configured to receive the measurements of (1) axial light loss, (2) intermediate angle scatter, (3) 90° polarized side scatter, (4) 90° depolarized side scatter, and (5) fluorescence from the plurality of detectors. The method also includes configuring the processor to perform a WBC differential analysis of the blood sample, based on all five measurements, for particles that emit fluorescence above a fluorescence threshold. The method may include configuring the processor to pre-screen the received measurements to remove from consideration any particles that do not meet the fluorescence threshold. The axial light loss detector may measure axial light loss at 0° scatter. The intermediate angle scatter detector may measure light angle scatter at about 3° to about 15°. The plurality of detectors may include one or more photomultiplier tubes. The method may also include configuring the excitation source to emit light at a wavelength corresponding to the fluorescent dye. Alternatively, the fluorescent dye may be selected to correspond with the excitation source. The fluorescent dye may be cell membrane permeable, and nucleic acid binding.

The method may further comprise configuring an incubation subsystem of the hematology analyzer to incubate the blood sample with a WBC reagent. The WBC reagent may include the fluorescent dye and a lysing agent. Alternatively, the WBC reagent may include (a) at least one surfactant, (b) at least one buffer or at least one salt, (c) at least one antimicrobial agent, and (d) the fluorescent dye. The incubation subsystem may be configured to incubate the blood sample with the WBC reagent for a period of time of less than about 25 seconds, less than about 17 seconds, or less than about 9 seconds. The incubation subsystem may also be configured to incubate the blood sample with the WBC reagent at a temperature ranging from about 30° C. to about 50° C., such as about 40° C.

In another embodiment, there is provided a hematology analyzer for performing a WBC differential analysis, comprising: (1) means for exciting particles within a blood sample, which includes positioning a laser light source to excite the blood sample as it transverses a flowcell of the hematology analyzer, or equivalents thereof; (2) means for measuring a plurality of light scatter signals from the excited particles within the blood sample, which includes a plurality of detectors (as discussed above), or equivalents thereof; (3) means for measuring a fluorescence signal from the excited particles within the blood sample, which includes fluorescence detectors (as discussed above), or equivalents thereof; (4) means for screening the excited particles to remove from consideration any particles that do not meet a fluorescence threshold, which includes a processor configured with a fluorescence trigger (as discussed above), or equivalents thereof; and (5) means for performing a WBC differential analysis, based on the plurality of light scatter signals and the fluorescence signal, for the particles passing the means for screening, which includes a processor configured to perform a WBC differential (as discussed above), or equivalents thereof. The hematology analyzer may further comprise means for incubating the blood sample with a WBC reagent for an incubation period of less than about 25 seconds, which includes an incubation subsystem (as discussed above), or equivalents thereof. The hematology analyzer may further comprise means for incubating the blood sample with a WBC reagent at a temperature ranging from about 30° C. to about 50° C., which includes an incubation subsystem (as discussed above), or equivalents thereof.

In another embodiment, there is provided a method of performing a WBC analysis with an automated hematology analyzer. The method comprises: (a) diluting a sample of whole blood with a WBC reagent, wherein the WBC reagent includes a RBCs lysing agent and a fluorescent dye that penetrates WBC membranes and binds to WBC nucleic acids; (b) incubating the diluted blood sample of step (a) for an incubation period of less than about 25 seconds, at a temperature ranging from about 30° C. to about 50° C.; (c) delivering the incubated sample from step (b) to a flow cell in the hematology analyzer; (d) exciting the incubated sample from step (c) with an excitation source as the incubated sample traverses the flow cell; (e) collecting a plurality of light scatter signals and a fluorescence emission signal from the excited sample; and (0 performing a WBC differential based on all the signals collected in step (e), while removing from consideration any particles within the diluted blood sample that do not meet a fluorescence threshold based on the fluorescence emission signal. The WBC reagent may include (a) at least one surfactant, (b) at least one buffer or at least one salt, (c) at least one antimicrobial agent, and (d) at least one fluorescent dye. The excitation source may have a wavelength of from about 350 nm to about 700 nm. The fluorescence emission may be collected at a wavelength of from about 360 nm to about 750 nm, by a band-pass filter or a long-pass filter.

In yet another embodiment, there is provided a method for counting and classifying WBCs by means of an automated hematology analyzer, the method comprising the steps of: (a) diluting a sample of whole blood with at least one WBC reagent; (b) incubating the diluted sample of step (a) for sufficient period of time within a selected temperature range to lyse RBCs, to preserve WBCs, to allow at least one fluorescent dye to penetrate cell membranes of the WBCs, and bind nucleic acids within the nuclei of the WBCs; (c) delivering the incubated sample from step (b) to a flow cell in a stream; (d) exciting the incubated sample from step (c) by means of a source of light as the incubated sample traverses the flow cell; (e) collecting a plurality of optical scatter signals and at least one fluorescence emission signal simultaneously; and (f) differentiating and quantifying WBCs by means of the signals collected in step (e). Features of the embodiment include, but are not limited to: (1) use of at least one fluorescent dye to bind and stain nucleic acids in WBCs and other nuclei-containing cells in a given sample of blood during the procedure for lysing RBCs, and to induce fluorescent emissions upon excitation by photons from a given source of light, such as a laser beam at an appropriate wavelength; (2) use of a fluorescent trigger to separate and collect events that emit strong fluorescence (e.g., events involving WBCs and other nuclei-containing cells); (3) use of a plurality of optical channels and at least one channel for fluorescence for collecting data and analyzing the data so collected in order to identify each cell population and reveal additional information.

In yet another embodiment, the systems and methods disclosed herein include: (a) staining a blood sample with an exclusive, cell membrane permeable, fluorescent dye, which corresponds in emission spectrum to an excitation source of a hematology instrument; (b) using a fluorescence trigger to screen the blood sample for WBCs; and (c) using a combination of measurements to perform a differential analysis. The combination of measurements may include one or more measurements selected from the group consisting of: axial light loss, intermediate angle scatter, 90° polarized side scatter, 90° depolarized side scatter, one or more fluorescence emission measurements, multiple ring intermediate angle scatter, and any combinations or equivalents thereof.

In one embodiment, the invention is directed toward one or more computer systems capable of carrying out the functionality described herein. For example, any of the method/analysis steps discussed herein may be implemented in a computer system having one or more processors, a data communication infrastructure (e.g., a communications bus, cross-over bar, or network), a display interface, and/or a storage or memory unit. The storage or memory unit may include computer-readable storage medium with instructions (e.g., control logic or software) that, when executed, cause the processor(s) to perform one or more of the functions described herein. The terms "computer-readable storage medium," "computer program medium," and "computer usable medium" are used to generally refer to media such as a removable storage drive, removable storage units, data transmitted via a communications interface, and/or a hard disk installed in a hard disk drive. Such computer program products provide computer software, instructions, and/or data to a computer system, which also serve to transform the computer system from a general purpose computer into a special purpose computer programmed to perform the particular functions described herein. Where appropriate, the processor, associated components, and equivalent systems and sub-systems thus serve as examples of "means for" performing select operations and functions. Such "means for" performing select operations and functions also serve to transform a general purpose computer into a special purpose computer programmed to perform said select operations and functions.

Conclusion

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

The above Detailed Description refers to the accompanying drawings that illustrate one or more exemplary embodiments. Other embodiments are possible. Modifications may be made to the embodiment described without departing from the spirit and scope of the present invention. Therefore, the Detailed Description is not meant to be limiting. Further, the Summary and Abstract sections may set forth one or more, but not all exemplary embodiments of the present invention as contemplated by the inventor(s), and thus, are not intended to limit the present invention and the appended claims in any way.

What is claimed is:
1. A hematology analyzer for conducting a white blood cell (WBC) differential analysis on a blood sample that contains a plurality of WBCs, the analyzer comprising:
   an excitation source positioned to excite particles within the blood sample;
   a plurality of detectors including (1) an axial light loss detector positioned to measure axial light loss from the excited blood sample, (2) an intermediate angle scatter detector positioned to measure intermediate angle scatter from the excited blood sample, (3) a polarized side scatter detector positioned to measure 90° polarized side scatter from the excited blood sample, (4) a depolarized side scatter detector positioned to measure 90° depolarized side scatter from the excited blood sample, and (5) a fluorescence detector positioned to measure fluorescence emitted from the excited blood sample;
   a processor; and
   a non-transitory computer-readable memory medium comprising instructions that when executed cause the processor to:
      (a) dilute the blood sample with a WBC reagent that includes a red blood cell (RBC) lysing agent and a cell membrane permeable, nucleic acid binding fluorescent dye;
      (b) incubate the diluted blood sample of step (a) for an incubation period of time;
      (c) deliver the incubated sample from step (b) to a flow cell in the hematology analyzer;
      (d) excite the incubated sample from step (c) with an excitation source as the incubated sample traverses the flow cell;
      (e) collect a plurality of light scatter signals and fluorescence emission signals from the excited sample;

(f) prior to performing a WBC differential analysis, exclude nuclei-free events and retain nuclei-containing events using only a fluorescence trigger that is limited to fluorescence emission signals and is set to a fluorescence magnitude that is greater than fluorescence emission signals from RBCs, including RBC fragments, and is less than fluorescence emission signals from WBCs; and (g) perform the WBC differential analysis on the nuclei-containing events collected in step (f).

2. The hematology analyzer of claim 1, wherein the axial light loss detector measures axial light loss at 0° scatter.

3. The hematology analyzer of claim 1, wherein the intermediate angle scatter detector measures light angle scatter at about 3° to about 15°.

4. The hematology analyzer of claim 1, wherein the plurality of detectors include one or more photomultiplier tubes.

5. The hematology analyzer of claim 1, wherein the excitation source is a laser.

6. The hematology analyzer of claim 5, wherein the laser is configured to emit light at a wavelength corresponding to the fluorescent dye.

7. The hematology analyzer of claim 1, wherein the fluorescent dye is selected to correspond with the excitation source, and wherein the fluorescent dye is cell membrane permeable, and nucleic acid binding.

8. The hematology analyzer of claim 1, further comprising:

an incubation subsystem for diluting the blood sample with a WBC reagent.

9. The hematology analyzer of claim 8, wherein the WBC reagent includes the fluorescent dye and a lysing agent.

10. The hematology analyzer of claim 8, wherein the WBC reagent includes (a) at least one surfactant, (b) at least one buffer or at least one salt, (c) at least one antimicrobial agent, and (d) the fluorescent dye.

11. The hematology analyzer of claim 8, wherein the incubation subsystem is configured to incubate the blood sample with the WBC reagent for a period of time of less than 25 seconds.

12. The hematology analyzer of claim 8, wherein the incubation subsystem is configured to incubate the blood sample with the WBC reagent for a period of time of less than 17 seconds.

13. The hematology analyzer of claim 8, wherein the incubation subsystem is configured to incubate the blood sample with the WBC reagent for a period of time of less than 9 seconds.

14. The hematology analyzer of claim 8, wherein the incubation subsystem is configured to incubate the blood sample with the WBC reagent at a temperature ranging from 30° C. to 50° C.

15. The hematology analyzer of claim 8, wherein the incubation subsystem is configured to incubate the blood sample with the WBC reagent at a temperature of 40° C.

* * * * *